(12) United States Patent
Bond et al.

(10) Patent No.: US 8,818,057 B2
(45) Date of Patent: Aug. 26, 2014

(54) METHODS AND APPARATUS FOR REGISTRATION OF MEDICAL IMAGES

(75) Inventors: Sarah Bond, Oxford (GB); Timor Kadir, Oxford (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 990 days.

(21) Appl. No.: 12/842,348

(22) Filed: Jul. 23, 2010

(65) Prior Publication Data
US 2011/0019885 A1 Jan. 27, 2011

(30) Foreign Application Priority Data
Jul. 24, 2009 (GB) .................................. 0912845.5

(51) Int. Cl.
*G06K 9/46* (2006.01)
(52) U.S. Cl.
USPC ........................................... 382/128; 382/294
(58) Field of Classification Search
None
See application file for complete search history.

(56) References Cited

U.S. PATENT DOCUMENTS

| | | | | |
|---|---|---|---|---|
| 2001/0036302 A1* | 11/2001 | Miller | ........................... | 382/128 |
| 2007/0047840 A1* | 3/2007 | Xu et al. | ....................... | 382/294 |
| 2007/0179377 A1* | 8/2007 | Carlsen et al. | ................ | 600/407 |
| 2008/0019580 A1 | 1/2008 | Ohyu et al. | | |
| 2009/0135191 A1 | 5/2009 | Azar et al. | | |
| 2011/0019889 A1* | 1/2011 | Gering et al. | ................. | 382/131 |

FOREIGN PATENT DOCUMENTS

| | | |
|---|---|---|
| WO | WO 2009/072050 | 6/2009 |
| WO | WO 2009/077938 | 6/2009 |
| WO | WO 2009072050 A1 * | 6/2009 |
| WO | WO 2010/015957 | 2/2010 |

OTHER PUBLICATIONS

"Nonrigid Registration Using Free-Form Deformations: Application to Breast MR Images," Rueckert et al., IEEE Trans. on Medical Imaging, vol. 18, No. 8 (1999) pp. 712-721.

* cited by examiner

*Primary Examiner* — Elaine Gort
*Assistant Examiner* — Gregory Lultschik
(74) *Attorney, Agent, or Firm* — Schiff Hardin LLP

(57) ABSTRACT

In methods and an apparatus for registering two medical images of a subject, a first image is compared with a first anatomical atlas and a second image with a second anatomical atlas, to generate labels for anatomical features in each image. The first anatomical atlas has at least two anatomical features in common with the second, and each label includes a suggested location of the anatomical feature to which it relates. A number of labels are identified for each image, and a value of a similarity function between labels of the respective images is calculated. The two images are registered based on the value of the similarity function.

15 Claims, 2 Drawing Sheets

METHODS AND APPARATUS FOR REGISTRATION OF MEDICAL IMAGES

BACKGROUND OF THE INVENTION

1. Field of the Invention

This invention is directed to methods and apparatus for registration of medical images of a subject.

2. Description of the Prior Art

The registration of medical images is a useful and sometime necessary precursor to their analysis and review. For example, for treatment monitoring, restaging or follow-up of lung cancer cases, the clinician may have available a number of previous FDG-PET/CT scans with which to compare the current scan. Registration techniques are able to provide the correspondence of locations in such, so-called, longitudinal studies. This correspondence may be used, for example, to link the cross-hairs of a multi-volume display allowing the clinician to compare similar anatomical locations easily and to assess changes therein. Registration of medical volumes may involve rigid or non-rigid (deformable) transformations and single or multiple modalities. Such algorithms operate typically by optimising a similarity function under the constraint of a particular transformation model. For example, for multi-modality deformable registration, gradient descent can be used to optimise a B-spline transformation model under a Mutual Information similarity function, for example as described in "Non-rigid registration of breast MR images using mutual information", D. Rueckert, C. Hayes, C. Studholme, P. Summers, M. Leach, and D. J. Hawkes, In First Int. Conf. on Medical Image Computing and Computer-Assisted Intervention (MICCAI 1998), Lecture Notes in Computer Science, pages 1144-1152, Cambridge, Mass., 1998. Springer-Verlag.

In certain embodiments, this invention is concerned with deformable registration algorithms. One of the key steps in such algorithms is their initialisation. This is especially crucial if gradient descent is used to optimise the transformation. Where both volumes are of the same patient and are taken across a similar field-of-view (FOV), covering the same area of the body and the amount of deformation is small the initialisation may be achieved simply by aligning the centres of the volumes or alternatively their centres of mass. Hybrid systems (PET/CT, SPECT/CT, MR-PET) rely on mechanical calibration of the joint devices to provide the initial alignment. However, where the FOVs are substantially different and when the images have not been acquired on a hybrid scanner, or in cases where the deformation is large such an approach will not work and the subsequent registration step will fail, as the optimisation algorithm will most probably fall into an irrelevant local minimum.

A number of automated approaches have been proposed to date. One way to perform the initialisation is to do a so-called axis search. Here, the volume with the smaller field of view is translated across the larger volume along the centre of the three axis dimensions x, y and Z. The location at which the similarity function is maximised is chosen as the initial alignment. The methods works in some cases but can give an incorrect result where there is a degree of size difference or rotation between the objects in the images.

A more general approach is to use a low dimensional transformation such as a rigid or affine registration step prior to applying the deformable registration. The method can also work where the degree of initial deformation is small but will fail where degree of change is greater.

An alternative approach is to use a feature based registration algorithm prior to running the main registration approach. Here, a feature detector selects a set keypoints or interest points in both images and a matching algorithm such as RANSAC or robust ICP is used to estimate their correspondence and hence transformation between the interest points. Such techniques can work well but cannot always find a good match when only a small subset of the features are visible in both images and are reliant on the detection of a large number of interest points.

Yet another alternative approach solves the problem by first fitting an anatomical atlas to each image using the anatomical information to initialise the deformable registration algorithm. The key idea is to detect the location of key anatomical features which allows the approximate initial position to be determined in a straightforward and robust manner. For example, in previously considered methods, the centres of the hips, and the base point of the coccyx were used as initial points for alignment. This is in contrast to the generic interest points used previously which detect only features that have particular intensity profiles—edges, corners and so forth. The problem with such an approach is that it relies on the fitting of the anatomical atlas to be perfectly correct. Mislabelled features will cause the algorithm to fail catastrophically.

SUMMARY OF THE INVENTION

The present invention aims to address these problems and provide improvements upon the known devices and methods.

In general terms, one embodiment of a first aspect of the invention is a method of registering two medical images of a subject including the steps of: comparing a first image with a first anatomical atlas and comparing a second image with a second anatomical atlas, to generate labels for anatomical features in each image, wherein the first anatomical atlas has at least two anatomical features in common with the second, and wherein each label includes a suggested location of the anatomical feature to which it relates; identifying a number of labels for each image; calculating a value of a similarity function between labels of the first image and labels of the second image; and registering the two images based on the value of the similarity function.

This provides an assessment of the quality of the labels of the atlases, before the registration step is performed, thus allowing for a more robust registration.

Preferably, the step of identifying includes identifying a number of pairs of labels, wherein each pair includes a label for the first image and a label for the second image, and the step of calculating includes calculating a value of the similarity function between pairs of labels.

Suitably, the method further includes identifying a best pair of labels, the best pair having the best value of the similarity function calculated.

This allows the method to find the best fitting labels, rather than simply using the two atlases without any assessment of their accuracy.

More preferably, the step of identifying includes identifying a plurality of sets of labels for each image, and wherein the step of calculating includes calculating a value of the similarity function between pairs of sets.

Suitably, the step of identifying a best pair includes identifying a best pair of sets, the best pair having the best value of the similarity function calculated.

In one embodiment, the method further includes calculating a geometric transformation necessary to align one label or set, as the case may be, of the best pair with the other label or set of the best pair.

Suitably, the method further includes applying the geometric transformation to one of the images.

Preferably, each label in each set relates to a different anatomical feature.

In one embodiment, the two medical images are from the same medical imaging modality. In another, the two medical images are from different medical imaging modalities.

In an embodiment, the step of calculating the similarity function between pairs of sets includes a regularizer.

Preferably, the similarity function includes intensity information and spatial location information.

Suitably, the method further includes identifying the specific anatomical feature associated with respective labels, wherein the similarity function is based in part on assessment of the similarity of the anatomical features identified for the respective labels.

In an embodiment, the two images have different but overlapping fields of view.

In general terms, one embodiment of a second aspect of the invention is an apparatus for registration of two medical images of a subject, the apparatus including: a processor adapted to compare a first image with a first anatomical atlas and to compare a second image with a second anatomical atlas, to generate labels for anatomical features in each image, wherein the first anatomical atlas has at least two anatomical features in common with the second, and wherein each label includes a suggested location of the anatomical feature to which it relates; identify a number of labels for each image; calculate a value of a similarity function between labels of the respective images; and register the two images based on the value of the similarity function; and a display device in communication with the processor that is adapted to display the registered images.

In general terms, one embodiment of a third aspect of the invention is a method of registering two images includes the steps of: comparing a first image with a first anatomical atlas and comparing a second image with a second anatomical atlas, to generate a number of labels for each anatomical feature in each image, wherein the first anatomical atlas may be the same or different from the second anatomical atlas, but must have at least two features in common, and wherein each label includes a suggested location of the anatomical feature to which it relates; identifying a plurality of sets of labels for each image, wherein each label in each set relates to a different anatomical feature; calculating a value of a similarity function between a number of pairs of sets, wherein each pair includes a set of labels for the first image and a set of labels for the second image; identifying the pair of sets having the best value of the similarity function calculated (the Best Pair of Sets); calculating a (the) geometric transformation necessary to align one of the Best Pair of Sets with the other of the Best Pair of Sets and applying said geometric transformation to the whole of one of the images.

In general terms, one embodiment of a fourth aspect of the invention is a non-transitory computer-readable storage medium encoded with program code is stored that, when loaded into or run on a computer, to cause the computer to become apparatus, or to implement a method, according to the aspects described above.

The above aspects and embodiments may be combined to provide further aspects and embodiments of the invention.

DESCRIPTION OF THE PREFERRED EMBODIMENTS

When the following terms are used herein, the accompanying definitions can be applied:
PET—Positron Emission Tomography
SUV—Standardised Uptake Value
MRI—Magnetic Resonance Imaging
ROI—Region of interest
FOV—Field of View Embodiments of the present invention can address problems in the previously considered methods by calculating a similarity function between anatomical atlas labels of the first image and labels of the second image, and registering the two images based on the value of the similarity function, allowing a qualitative measure of the match between the atlases, rather than a simple assumption that the two should fit. Embodiments also allow the use of two different atlases, or image areas, as long as the atlases/image areas overlap to some extent.

One technical problem addressed by this invention is the initialization and execution of deformable registration for images with large deformations. In one embodiment, the invention is based on the previously suggested approach of fitting an anatomical atlas to a pair of images and using the features to perform the initial match. It addresses the failure problems associated with this technique through a series of modifications and extensions, described later.

First, this section provides some background to the type of anatomical models used in embodiments of this invention.
The Anatomical Atlas:

One known technique that could be used for this purpose is the so-called Pictorial Structure, for example as described in "The representation and matching of pictorial structures" (M. A. Fischler and R. A. Elschlager. IEEE Transactions on Computers, 22(1), pages 67-92. 1973) or "Pictorial structures for object recognition" (P. F. Felzenswalb and D. P. Huttenlocher. International Journal on Computer Vison, 61(1), pages 55-79, 2005. Proposed by Fischler and Elschlager, Pictorial Structures represent objects as a collection of parts, each with a model of its possible appearance in the image connected by a series of spring-like connections which constrain their relative locations.

Figure 1:
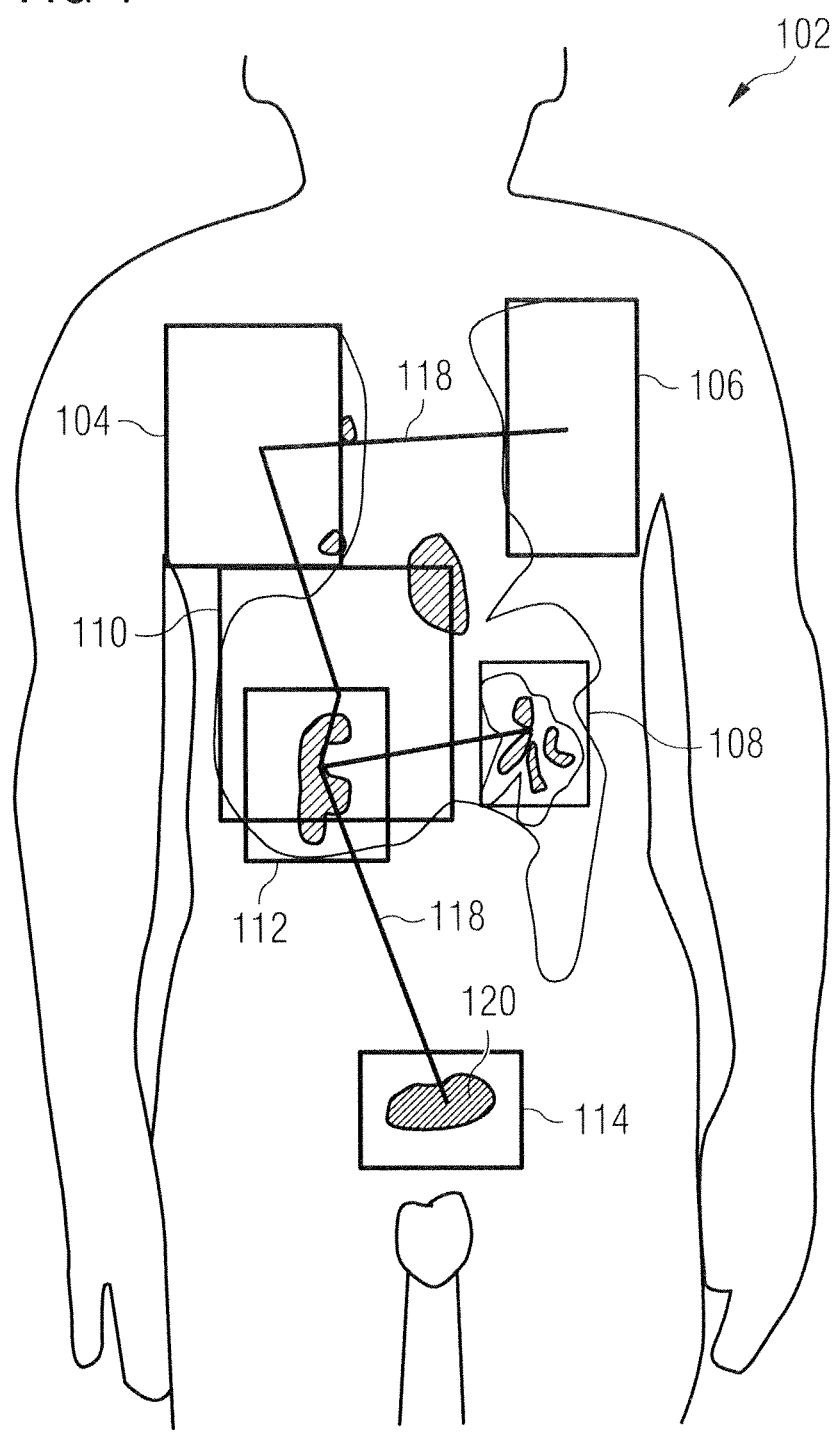
FIG. 1 is a diagram illustrating a model having a set of labels according to an embodiment of the invention.
Figure 2:
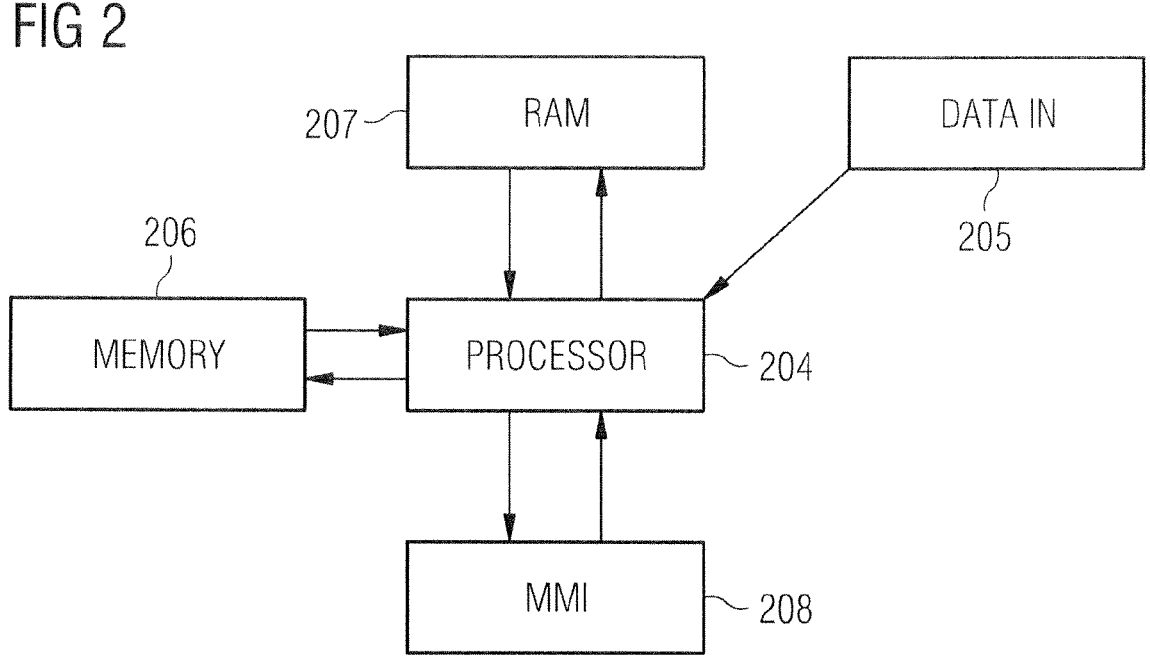
FIG. 2 is a diagram illustrating an apparatus according to an embodiment of the invention.

FIG. 1 shows an example where each of the boxes around each of the 6 organs represents one part of the model representing the lungs, liver, kidneys and bladder on a maximum intensity projection of a PET image (102). The boxes 104, 106, 108, 110, 112, 114 each surround a respective anatomical feature, for example box 114 is for the bladder 120. The boxes represent the parts and the lines 118 their spatial relationships. The appearance of each part can be modelled by any suitable method; the only requirement may be that it is able to produce a soft probability map. For example, each part can be modelled by its intensity distribution.

The spatial relationships can be modelled by some appropriate probability distribution such as a uniform or Gaussian. In the latter case, each pair of parts has a preferred relative position corresponding to the mean of the Gaussian with some degree of flexibility defined by the covariance matrix. In the example shown in FIG. 1 the relative position of the lungs would have a small variance in the vertical direction since it is rare to find people with lungs not in the same vertical position, but possibly larger variances in the horizontal direction. Here the spatial relationships are modelled in the form of a tree.

Alternatively, a more comprehensive model could use a partially or fully connected graph to encode the spatial relationships.

Such models can be fitted to a novel image using Belief Propagation algorithms either in their traditional form for graphs without loops (trees) or in a modified form to deal with graphs with cycles.

Initialization of Deformable Registration

In the previously considered methods, the authors find the best fit between the two atlases, and use the labels from this best fit to initialize the registration. As discussed above, such a scheme relies on the correct fitting of the anatomical atlas. To overcome this limitation an embodiment of the present invention samples from the pair of anatomical atlases and evaluates each possible pair of labelling according to a cost function. It then chooses the labelling and initial deformation according to minimum of the cost function.

The algorithm for this embodiment works as follows:

1. Fit anatomical atlas A to image 1 and anatomical atlas B to image 2
2. Sample N labellings from fitted atlas A and fitted atlas B. Note that these labelling are atlas features, for example the centre of the heart, or the centre points of the kidneys.
3. Evaluate the cost of each pair of labellings, using a similarity metric. This could be Sum Squared Difference, or a Correlation-based metric, or a Mutual Information based metric. The choice of metric depends on whether the 2 images to be aligned are from the same or from different imaging modalities (e.g. PET, SPECT, CT, MRI.)
4. Choose the pairs of labellings and corresponding deformation that gives rise to the minimum cost.
5. Initialize the deformable registration using selected deformation and perform the deformable registration.

In this (and other) embodiments, the images 1 and 2 may have different but overlapping fields of view. As long as the atlases overlap to a certain degree (for example, by having at least two common anatomical feature labels), the comparison between the atlas labels can be made. For example, if one image is of the whole body, and another of the brain, a registration can still be performed, assuming the body atlas and the brain atlas share common feature labels.

In general terms, for the steps above (and in other embodiments) it is not necessary for the labels to have been identified as relating to a specific feature (e.g. heart) before the comparisons are made. Indeed, it is not even necessary for the labels to have been identified as correct—the method identifies the best matching labels.

The labels may be compared in groups. For example, a group of four labels in a square in image 1 may be compared with a number of labels in image 2, not necessarily known to form a square. The labels in image 2 may number more or fewer than four—for example, if only three relevant labels are listed, these can still be matched to the square in image 1 if the positions are of sufficiently low cost at three of the "corners".

The cost function can include several terms. For example, one simple cost function could just consider the similarity function that arises from applying the deformation that the labellings induce. For example, if the anatomical atlas fitted to both images comprised the model shown in FIG. 1 then a deformable transformation can be fitted to each of the N selected labellings supplied by the fitted atlas and the similarity function evaluated. The same deformation model may be used to fit the supplied correspondences or a different model may be used. Since the correspondences arising from the anatomical atlas tend to be sparse, an interpolating step must also be performed.

An example of evaluating the cost function for 2 images just using the similarity is given in the table below. There are 7 labels in the atlas fitted to image 1 ($I_1$) and 9 labels in the atlas fitted to image 2 ($I_2$). Looking at the similarity metrics between the two sets of labels, the minimum cost labels are taken as pairs to initialize the registration. These are highlighted in the table.

In this case the cost function is given by:

Cost=sum(similarity between pairs)/(#pairs)=0.7/6=0.12.

This cost can incur various restrictions, for example it must contain a minimum number of pairs, or it must be less than a certain value, and should be normalized according to the number of pairs considered.

|        | $I_1$-1 | $I_1$-2 | $I_1$-3 | $I_1$-4 | $I_1$-5 | $I_1$-6 | $I_1$-7 |
|--------|---------|---------|---------|---------|---------|---------|---------|
| $I_2$-1 | 0.1 | 0.7 | 1.0 | 0.4 | 0.5 | 0.8 | 0.6 |
| $I_2$-2 | 0.8 | 0.3 | 0.0 | 0.9 | 0.8 | 0.8 | 0.7 |
| $I_2$-3 | 0.7 | 0.6 | 0.9 | 0.7 | 0.8 | 0.4 | 0.8 |
| $I_2$-4 | 0.3 | 0.5 | 0.7 | 0.1 | 0.3 | 0.5 | 0.7 |
| $I_2$-5 | 0.6 | 0.1 | 0.9 | 0.5 | 0.8 | 0.6 | 0.6 |
| $I_2$-6 | 0.5 | 0.8 | 0.6 | 0.7 | 0.6 | 0.9 | 0.4 |
| $I_2$-7 | 0.6 | 0.9 | 0.5 | 0.5 | 0.5 | 0.6 | 0.2 |
| $I_2$-8 | 0.8 | 0.4 | 0.8 | 0.8 | 0.7 | 0.6 | 0.9 |
| $I_2$-9 | 0.9 | 0.4 | 0.8 | 0.7 | 0.2 | 0.5 | 0.8 |

A more complex cost function will consider the whole series of pairs together and the deformation which results from a given series of pairs. Such a cost will then use a similarity measure and a regularizer. This regularization can be based on the distance transform, which would constrain pairs to be positioned correctly relative to each other. Such a regularizer would, for example, not allow the left and right lung to be swapped even if they look similar according to the pairs.

This more complex method will minimize the cost function:

Cost=Similarity between pairs+regularization

Therefore if a set of pairs are similar, but involve large deformations, the cost will be high. For a low cost, the pairs must be similar AND correspond to an allowable deformation.

The cost function can also include further terms to measure the quality of the labellings: the likelihood of the labelling in each pair of atlases, the complexity if the induced transformation.

Other techniques can be used to fit the anatomical atlas. For example, direct discriminative methods can be built from training data which detect the anatomical regions or object in the image without a spatial model.

An additional step that would enhance the subsequent registration algorithm is to include the cost of the anatomical atlas to the similarity function. This would ensure that the resulting deformation tends towards solutions that are valid for both the anatomical atlas and the similarity function—that is the resulting deformation matches corresponding anatomical locations and locations with similar appearances. To make this work, at each step of the registration the cost of the pair of anatomical atlases arising from the current deformation estimate is evaluated and added to the similarity cost function. For gradient descent based algorithms that use closed-form derivatives of the similarity function the gradient of the anatomical atlas may be evaluated.

For example, a label for image 1 identified as a lung label may only need to be compared to the identified lung label of image 2. In other cases, the identified lung label may in any case be compared to all labels of image 2.

In alternative embodiments, the two images may of course originate from the same modality, rather than different modalities such as PET/CT, SPECT/CT, MR-PET. The anatomical atlas may be placed on the respective images manually, or by a known automatic location method.

It will be appreciated by those skilled in the art that the invention has been described by way of example only, and that a variety of alternative approaches may be adopted without departing from the scope of the invention, as defined by the appended claims.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for registering two medical images of a subject, comprising:
providing a first medical image and a second medical image to a computerized processor and, from said processor, accessing an electronic memory arrangement in which a first anatomical atlas and a second anatomical atlas are stored, said first anatomical atlas having at least two anatomical features in common with said second anatomical atlas;
in said processor, comparing said first medical image with said first anatomical atlas to identify a plurality of first labels respectively relating to anatomical features in said first medical image;
in said processor comparing said second medical image with said second anatomical atlas to identify a plurality of second labels respectively relating to anatomical features in said second medical image;
in said processor, automatically calculating a value of a similarity metric, that represents a degree of similarity, between said first labels and said second labels;
in said processor, bringing said first medical image and said second medical image into registration with each other based on the value of the similarity metric;
in said processor, identifying a plurality of sets of first labels from among said plurality of first labels, wherein each of the plurality of sets of first labels contains a plurality of first labels;
in said processor, identifying a plurality of sets of second labels from among said plurality of second labels, wherein each of the plurality of sets of second labels contains a plurality of second labels;
wherein the number of first labels within the set of first labels is different from the number of second labels within the set of second labels;
in said processor, identifying pairs of sets of labels, each pair of sets of labels comprising a set of said first labels and a set of said second labels;
in said processor, calculating said value of said similarity metric between said set of first labels and said set of second labels in each said pair; and
making the first medical image and the second medical image brought into registration with each other available at an output of said processor in electronic form, as a data file.

2. A method according to claim 1 comprising:
in said processor, identifying a plurality of pairs of labels, each pair of label comprising one of said first labels and one of said second labels; and
in said processor, calculating said value of said similarity metric between respective first and second labels in the respective pairs of labels.

3. A method according to claim 2, comprising:
in said processor, automatically designating one of said pairs of labels as a most similar pair that has a value of said similarity metric that indicates a highest degree of similarity between the first label and the second label in said one of said pairs; and
bringing said first and second medical image into registration with each other using the value of the similarity metric for said most similar pair of labels.

4. A method as claimed in claim 3 comprising
calculating said similarity metric using a cost function, and designating said one of said pairs that has a lowest value of said cost function as said most similar pair of labels.

5. A method as claimed in claim 3 comprising:
in said processor, calculating a geometric transformation that is necessary to align one label in said most similar pair of labels with the other label in said most similar pair of labels; and
bringing said first medical image and said second medical image into registration with each other by applying said geometric transformation to one of said first and second medical images.

6. A method as claimed in claim 1 comprising:
in said processor, designating one of said pairs of sets of labels as a most similar pair of sets of labels, that has a value of said similarity metric indicating a highest degree of similarity between the set of first labels and the set of second labels thereof; and
in said processor, bringing said first medical image and said second medical image into registration with each other using the similarity metric of said most similar pair of sets of labels.

7. A method as claimed in claim 6 comprising
calculating said similarity metric using a cost function, and designating said one of said pairs of sets of labels that has a lowest value of said cost function, as said most similar pair of sets of labels.

8. A method as claimed in claim 7 comprising, in said processor, calculating said cost function with inclusion of a regularizer.

9. A method as claimed in claim 6 comprising:
in said processor, calculating a geometric transformation necessary to align one of the sets of labels in said most similar pair of sets of labels with the other set of labels in said most similar pair of sets of labels; and
bringing said first and second medical image into registration with each other by applying said geometric transformation to one of said first and second medical images.

10. A method as claimed in claim 1 comprising
identifying each of said sets of first labels and said sets of second labels so that each of label in each set relates a different anatomical feature.

11. A method as claimed in claim 1 comprising:
providing said first medical image to said processor acquired from a first medical imaging apparatus according to a first medical imaging modality, and providing said second medical image to said processor as a medical image acquired from a second medical imaging apparatus according to a second medical imaging modality that differs from said first medical imaging modality.

12. A method as claimed in claim 1 comprising
providing said first medical image to said processor as a medical image acquired from a first medical imaging apparatus according to a medical imaging modality, and providing said second medical image to said processor as a medical image acquired from a second medical imaging apparatus according to said medical imaging modality.

13. A method as claimed in claim 1 comprising
calculating said similarity metric in said processor using a similarity function comprising intensity information and spatial location information respectively from said first and second medical images.

14. An apparatus for registration of two medical images of a subject, said apparatus comprising:
a processor having an input configured to receive a first medical image and a second medical image;
said processor being configured to access an electronic memory arrangement in which a first anatomical atlas and a second anatomical atlas are stored, said first anatomical atlas having at least two anatomical features in common with said second anatomical atlas;
said processor being configured to compare said first medical image with said first anatomical atlas to identify a plurality of first labels respectively relating to anatomical features in said first medical image;
said processor being configured to compare said second medical image with said second anatomical atlas to identify a plurality of second labels respectively relating to anatomical features in said second medical image;
said processor being configured to automatically calculate a value of a similarity metric, that represents a degree of similarity, between said first labels and said second labels;
said processor being configured to bring said first medical image and said second medical image into registration with each other based on the value of the similarity metric;
said processor being configured to identify a plurality of sets of first labels from among said plurality of first labels, wherein each of the plurality of sets of first labels contains a plurality of first labels;
said processor being configured to identify a plurality of sets of second labels from among said plurality of second labels, wherein each of the plurality of sets of second labels contains a plurality of second labels;
wherein the number of first labels within the set of first labels is different from the number of second labels within the set of second labels;
said processor being configured to identify pairs of sets of labels, each pair of sets of labels comprising a set of said first labels and a set of said second labels;
said processor being configured to calculate said value of said similarity metric between said set of first labels and said set of second labels in each said pair; and
said processor being configured to make the first medical image and the second medical image brought into registration with each other available at an output of said processor in electronic form, as a data file.

15. A non-transitory, computer-readable data storage medium encoded with programming instructions, said storage medium being loaded into a computerized processor and said programming instructions causing said computerized processor to:
receive a first medical image and a second medical image;
access an electronic memory arrangement in which a first anatomical atlas and a second anatomical atlas are stored, said first anatomical atlas having at least two anatomical features in common with said second anatomical atlas;
compare said first medical image with said first anatomical atlas to identify a plurality of first labels respectively relating to anatomical features in said first medical image;
compare said second medical image with said second anatomical atlas to identify a plurality of second labels respectively relating to anatomical features in said second medical image;
calculate a value of a similarity metric, that represents a degree of similarity, between said first labels and said second labels;
bring said first medical image and said second medical image into registration with each other based on the value of the similarity metric;
identify a plurality of sets of first labels from among said plurality of first labels, wherein each of the plurality of sets of first labels contains a plurality of first labels;
identify a plurality of sets of second labels from among said plurality of second labels, wherein each of the plurality of sets of second labels contains a plurality of second labels;
wherein the number of first labels within the set of first labels is different from the number of second labels within the set of second labels;
identify pairs of sets of labels, each pair of sets of labels comprising a set of said first labels and a set of said second labels;
calculate said value of said similarity metric between said set of first labels and said set of second labels in each said pair; and
make the first medical image and the second medical image brought into registration with each other available at an output of said processor in electronic form, as a data file.

* * * * *